(12) United States Patent
Miyaji (10) Patent No.: US 8,242,043 B2
(45) Date of Patent: Aug. 14, 2012

(54) PROCESS FOR PRODUCTION OF SUPPORTED CATALYST FOR ACETIC ACID PRODUCTION

(75) Inventor: Atsuyuki Miyaji, Oita (JP)

(73) Assignee: Showa Denko K.K., Tokyo (JP)

( * ) Notice: Subject to any disclaimer, the term of this patent is extended or adjusted under 35 U.S.C. 154(b) by 788 days.

(21) Appl. No.: 12/298,283

(22) PCT Filed: Jun. 4, 2007

(86) PCT No.: PCT/JP2007/061677
§ 371 (c)(1),
(2), (4) Date: Oct. 23, 2008

(87) PCT Pub. No.: WO2007/145151
PCT Pub. Date: Dec. 21, 2007

(65) Prior Publication Data
US 2011/0054214 A1    Mar. 3, 2011

(30) Foreign Application Priority Data
Jun. 13, 2006   (JP) .................................. 2006-163540

(51) Int. Cl.
| | | |
|---|---|---|
| B01J 27/00 | (2006.01) |
| B01J 27/198 | (2006.01) |
| B01J 27/188 | (2006.01) |
| B01J 27/19 | (2006.01) |
| B01J 27/192 | (2006.01) |
| B01J 27/185 | (2006.01) |
| B01J 27/182 | (2006.01) |
| B01J 27/057 | (2006.01) |
| B01J 27/02 | (2006.01) |
| B01J 27/047 | (2006.01) |
| B01J 27/051 | (2006.01) |
| B01J 27/049 | (2006.01) |
| B01J 27/043 | (2006.01) |
| B01J 27/045 | (2006.01) |

(52) U.S. Cl. ........ 502/208; 502/209; 502/210; 502/211; 502/212; 502/213; 502/214; 502/215; 502/216; 502/219; 502/220; 502/221; 502/222; 502/223

(58) Field of Classification Search .......... 502/208–216, 502/219–223
See application file for complete search history.

(56) References Cited

U.S. PATENT DOCUMENTS

| | | | | |
|---|---|---|---|---|
| 2003/0092936 A1* | 5/2003 | Sano | .............................. | 562/538 |
| 2006/0052240 A1* | 3/2006 | Sakai | .............................. | 502/202 |
| 2007/0173663 A1* | 7/2007 | Miyaji et al. | .................. | 562/542 |

FOREIGN PATENT DOCUMENTS

| | | |
|---|---|---|
| CN | 1378482 A | 11/2002 |
| EP | 1 157 739 A1 | 11/2001 |
| EP | 1157739 A1 | 11/2001 |
| EP | 1226868 A1 | 7/2002 |
| KR | 2001-0102372 A | 11/2001 |

* cited by examiner

*Primary Examiner* — Patricia L Hailey
(74) *Attorney, Agent, or Firm* — Sughrue Mion, PLLC (57) ABSTRACT

A process for production of a supported catalyst that, when used for production of lower aliphatic carboxylic acids from oxygen and lower olefins, improves yields of the lower aliphatic carboxylic acids and minimizes production of carbon dioxide gas ($CO_2$) by-product compared to the prior art. A compound comprising at least one element selected from elements of Groups 8, 9 and 10 of the Periodic Table, at least one chloride of an element selected from copper, silver and zinc, and a chloroauric acid salt, are loaded on a carrier, after which there are further loaded a compound comprising at least one element selected from gallium, indium, thallium, germanium, tin, lead, phosphorus, arsenic, antimony, bismuth, sulfur, selenium, tellurium and polonium, and a heteropoly acid.

10 Claims, 2 Drawing Sheets

PROCESS FOR PRODUCTION OF SUPPORTED CATALYST FOR ACETIC ACID PRODUCTION

TECHNICAL FIELD

The present invention relates to a process for production of a supported catalyst, and to the use thereof. In particular, the invention relates to production of a supported catalyst that allows industrially advantageous production of lower aliphatic carboxylic acids such as acetic acid from oxygen and lower olefins such as ethylene in a gas phase, as well as to the use thereof.

BACKGROUND ART

Various methods for production of acetic acid from ethylene in a single-stage reaction have been proposed, for the numerous advantages in terms of industrial production steps and economy. For example, there have been disclosed a liquid-phase single-stage oxidation process using oxidation-reduction catalysts with metal ion pairs such as palladium-cobalt and palladium-iron (French Patent No. 1448361), processes using catalysts composed of palladium-phosphoric acid or sulfur-containing modifiers (Japanese Unexamined Patent Publication No. 47-013221, Japanese Unexamined Patent Publication No. 51-029425), and a gas-phase single-stage oxidation process using a catalyst composed of a three-component oxygen compound (Japanese Examined Patent Publication No. 46-006763). As a method for producing acetic acid using a catalyst comprising a palladium compound and a heteropoly acid, there has been proposed a gas-phase single-stage oxidation process using palladium phosphovanadomolybdate (Japanese Unexamined Patent Publication No. 54-57488).

Recently, as catalysts for obtaining acetic acid from ethylene and oxygen there have been proposed catalysts having palladium metal and an element of Group 14, 15 or 16 of the Periodic Table supported on a carrier (Japanese Unexamined Patent Publication No. 11-347412). These supported catalysts are prepared by the following steps.

First step: A step of loading a palladium-containing compound onto the carrier.
Second step: A step of alkali treatment.
Third step: A step of reduction treatment of the palladium-containing compound to produce palladium metal.
Fourth step: A step of loading an element of Group 14, 15 or 16 of the Periodic Table.

"Eggshell-type" palladium catalysts are useful for such supported catalysts. Eggshell-type catalysts are catalysts having the palladium in the carrier positioned on the surface of the carrier. Because reaction substrates do not readily diffuse into the internal regions of catalyst carriers, the metal components supported in the carrier have low probability of contacting the reaction substrates, and therefore their contribution to the reaction is low. With eggshell types, the metal component is abundantly present on the carrier surface, so that the efficiency for the reaction is higher than with normal types, even with the same amount of metal component. One known production process for obtaining eggshell-type palladium catalysts comprises a step of alkali treatment with sodium metasilicate or the like (Japanese Unexamined Patent Publication No. 7-89896). Also, Japanese Unexamined Patent Publication No. 2000-308830 discloses a process for production of an eggshell-type palladium supported catalyst comprising a step of treatment with an alkaline earth metal salt such as barium hydroxide.

The production process for a catalyst for production of acetic acid disclosed in Japanese Unexamined Patent Publication No. 11-347412 has a step in which a third component is loaded after an alkali treatment step to asymmetrically load the metal component such as palladium on the carrier surface (eggshell formation). The catalyst obtained by this process has high catalytic activity, but is problematic in that the catalyst preparation process is long and catalyst deterioration occurs during the reaction. The present inventors have therefore pursued development of a simple preparation process for catalysts that can prevent deterioration while maintaining high activity.

Another factor is that carbon dioxide is generated as a by-product in acetic acid production processes involving reaction between ethylene and oxygen. For example, according to Japanese Unexamined Patent Publication No. 7-89896, the carbon dioxide selectivity is about 5%. Generation of carbon dioxide means a lower final yield of acetic acid. In recent years, it has become a major goal to minimize production of carbon dioxide from the viewpoint of preventing global warming and reducing the environmental load. From an industrial standpoint, expensive equipment investment and equipment operation and maintenance costs are necessary for treatment of carbon dioxide by-product. The present inventors therefore investigated methods of further reducing carbon dioxide by-product in the production of acetic acid.

DISCLOSURE OF THE INVENTION

It is a main object of the present invention to solve the aforementioned problems of the prior art. Specifically, the object is to provide a supported catalyst that when used for production of lower aliphatic carboxylic acids such as acetic acid from oxygen and lower olefins such as ethylene, improves the yield of the lower aliphatic carboxylic acids and minimizes production of carbon dioxide gas ($CO_2$) by-product compared to the prior art, as well as a process for its production.

As a result of diligent research on these problems, the present inventors have discovered a process for production of a supported catalyst characterized by loading (a) a compound comprising at least one element selected from elements of Groups 8, 9 and 10 of the Periodic Table (hereinafter referred to as (a) group compound), (d) at least one chloride of an element selected from copper, silver and zinc (hereinafter referred to as (d) group compound), and a chloroauric acid salt on a carrier, and further loading a compound comprising at least one element selected from gallium, indium, thallium, germanium, tin, lead, phosphorus, arsenic, antimony, bismuth, sulfur, selenium, tellurium and polonium (hereinafter referred to as (b) group compound) (this process will hereunder also be referred to as "catalyst preparation process"), and the present invention has thereupon been completed.

According to the invention, the "Periodic Table" is the Periodic Table according to the 1989 revised edition of Inorganic Chemical Nomenclature by the IUPAC.

Specifically, the invention relates to the following (1)-(12).

(1) A process for production of a supported catalyst to be used for production of a lower aliphatic carboxylic acid from a lower olefin and oxygen, characterized by comprising the following first, second and third steps in order.

First Step

A step of impregnating a carrier with a solution containing at least one compound comprising at least one element selected from elements of Groups 8, 9 and 10 of the Periodic Table (hereinafter referred to as (a) group compound), at least one chloride of an element selected from copper, silver and zinc (hereinafter referred to as (d) group compound), and a chloroauric acid salt, to obtain an impregnated carrier (A).

Second Step

A step of contacting the impregnated carrier (A) with an alkaline substance and a compound comprising at least one element selected from gallium, indium, thallium, germanium, tin, lead, phosphorus, arsenic, antimony, bismuth, sulfur, selenium, tellurium and polonium (hereinafter referred to as (b) group compound) to obtain impregnated carrier (B) (where the alkaline substance and the (b) group compound may be contacted with impregnated carrier (A) either simultaneously or separately).

Third Step

A step of contacting impregnated carrier (B) with a reducing substance to obtain supported catalyst (C).

(2) A process for production of a supported catalyst according to (1) above, which further comprises a step of loading at least one compound selected from heteropoly acids and their salts (hereinafter referred to as (c) group compound) on the carrier.

(3) A process for production of a supported catalyst according to (1) or (2) above, wherein the (d) group compound is zinc chloride.

(4) A process for production of a supported catalyst according to any one of (1) to (3) above, wherein the chloroauric acid salt is an alkali metal salt of chloroauric acid.

(5) A process for production of a supported catalyst according to any one of (1) to (4) above, wherein the (a) group compound is a compound comprising at least one element selected from ruthenium, osmium, rhodium, iridium, palladium and platinum.

(6) A process for production of a supported catalyst according to any one of (1) to (5) above, wherein the (b) group compound is a compound comprising at least one element selected from gallium, germanium, tin, lead, bismuth, selenium and tellurium.

(7) A process for production of a supported catalyst according to any one of (2) to (6) above, wherein the polyatom of the heteropoly acid and/or its salt as the (c) group compound is tungsten and/or molybdenum.

(8) A process for production of a supported catalyst according to any one of (2) to (7) above, wherein the heteroatom of the heteropoly acid and/or its salt as the (c) group compound is at least one element selected from phosphorus, silicon and boron.

(9) A process for production of a supported catalyst according to any one of (2) to (8) above, wherein the heteropoly acid and/or its salt as the (c) group compound is at least one compound selected from silicotungstic acid, phosphotungstic acid, silicomolybdic acid, phosphomolybdic acid and salts thereof.

(10) A supported catalyst for production of acetic acid by reaction between ethylene and oxygen, which is produced by a process according to any one of (1) to (9) above.

(11) A process for production of a lower aliphatic carboxylic acid by reaction between a lower olefin and oxygen, characterized by using a supported catalyst produced by a process according to any one of (1) to (9) above.

(12) A process for production of acetic acid by reaction between ethylene and oxygen, characterized by using a supported catalyst produced by a process according to any one of (1) to (9) above.

According to the invention, using a supported catalyst obtained by the process for production of a supported catalyst of the invention can increase productivity of lower aliphatic carboxylic acids and minimize carbon dioxide gas by-product generation in the production of lower aliphatic carboxylic acids by reaction between lower olefins and oxygen, thereby lowering production costs for lower aliphatic carboxylic acids such as acetic acid.

BEST MODE FOR CARRYING OUT THE INVENTION

Preferred modes of the invention will now be explained in detail, with the understanding that the invention is not limited only to these modes, and that various modifications may be made such as are within the spirit and scope of the invention.

The supported catalyst obtained by the production process of the invention can be suitably used as a catalyst for production of lower aliphatic carboxylic acids (preferably acetic acid) wherein lower olefins (preferably ethylene) and oxygen are reacted (preferably in a gas phase).

A preferred process for production of a supported catalyst according to the invention will now be explained in detail.

First the following first to third steps are carried out in order.

First Step

A step in which the carrier is impregnated with a solution containing an (a) group compound (for example, a Pd-containing compound), (d) group compound (for example, Zn chloride) and a chloroauric acid salt, to obtain impregnated carrier (A).

Second Step

A step in which the impregnated carrier (A) is contacted with an alkaline substance and a (b) group compound (for example, a Te-containing compound) to obtain impregnated carrier (B).

Third Step

A step in which the impregnated carrier (B) is contacted with a reducing substance (for example, hydrazine) for reduction treatment of the (a) group compound and (d) group compound to obtain supported catalyst (C).

As a fourth step, the supported catalyst (C) is loaded with a (c) heteropoly acid (for example, silicotungstic acid) and/or a salt thereof to obtain a supported catalyst.

In the first step, a solution of the (a) group compound and solutions of the (d) group compound and chloroauric acid salt may each be contacted separately with the carrier for impregnation, but from the viewpoint of simplifying the process, they are preferably contacted simultaneously as a single solution for the impregnation. In the case of separate contact, the (a) group compound is preferably contacted first. In this case, the (d) group compound and chloroauric acid salt may be contacted simultaneously.

In the second step, the alkaline substance and (b) group compound may be contacted simultaneously or separately with the impregnated carrier (A), but they are preferably contacted simultaneously from the viewpoint of simplifying the process. When contacted separately, the alkaline substance is preferably contacted first.

The supported catalyst for production of a lower aliphatic carboxylic acid, which is obtained by the process of the invention, more preferably also has a (c) group compound (heteropoly acid and/or a salt thereof) supported therein. Thus, a step of loading the (c) group compound is included within the first to third steps or before or after the steps, in a manner that does not impair the effect of the invention, but preferably there is provided a step (fourth step) in which the (c) group compound is loaded after the third step, as mentioned above.

<Carrier>

There are no particular restrictions on the carrier used for production of the supported catalyst of the invention, but porous substances commonly used as carriers are preferred. Specifically, there may be mentioned silica, silica-alumina, diatomaceous earth, montmorillonite and titania. Silica is more preferred.

The form of the carrier is also not particularly restricted. Specifically, there may be mentioned powder, globular and pellet forms. The reaction system employed may be selected as optimal for the reactor, for example.

There are also no particular restrictions on the sizes of the carrier particles. When production of the lower aliphatic carboxylic acid is carried out in a fixed bed tubular reactor for gas-phase reaction, and the carrier is globular, the particle diameters are preferably 1-10 mm and more preferably 2-8 mm. If the particle diameters are smaller than 1 mm for reaction with the supported catalyst packed into a tubular reactor, a significant pressure loss will be experienced when the gas is passed through, potentially making it impossible to achieve effective gas circulation. If the particle diameters are greater than 10 mm, the reactive gas will not be able to diffuse to the interior of the catalyst, potentially making it impossible for the catalytic reaction to proceed efficiently. The pore structure of the carrier preferably has pore diameters of 1-1000 nm, and more preferably 3-200 nm. The area-to-weight ratio of the carrier as measured by the BET method is preferably 30-700 $m^2/g$ and more preferably 50-300 $m^2/g$. The bulk density of the carrier is preferably 50-1000 g/l and more preferably 300-500 g/l.

<The (a) Group Compound>

The (a) group compound is a compound comprising at least one element selected from elements of Groups 8, 9 and 10 of the Periodic Table. Elements of Groups 8, 9 and 10 of the Periodic Table include iron, ruthenium, osmium, cobalt, rhodium, iridium, nickel, palladium and platinum, among which palladium, platinum and nickel are preferred, and palladium is more preferred.

The (a) group compound may be in any form. It may also be in the form of the compound containing the element of Group 8, 9 or 10 or in elemental form. That is, the element may be present in ionic form in the compound, or metallic, i.e. zero-valent form.

As (a) group compounds there may be mentioned palladium metal, platinum metal and nickel metal, halides such as palladium chloride, platinic chloride and nickel chloride, organic acid salts such as palladium acetate and platinum acetate, nitric acid salts such as palladium nitrate, platinum nitrate and nickel nitrate, or palladium oxide, nickel oxide, sodium tetrachloropalladate, potassium tetrachloropalladate and the like, as well as complexes having organic compounds such as acetylacetonato, nitrile and ammonium as ligands. Particularly preferred are sodium tetrachloropalladate, hexachloroplatinic acid, potassium tetrachloropalladate and palladium nitrate. These (a) group compounds may be used alone or in combinations of two or more.

The loaded state of the (a) group compound on the carrier is preferably an "eggshell-type" state. To obtain an eggshell-type supported catalyst, the method of loading the (a) group compound on the carrier may be any one that can result in an eggshell-type supported catalyst, without any particular restrictions. An eggshell-type catalyst is one type of distribution of an active component (for example, palladium metal) on carrier particles or in a compact, with virtually all of the active component being present near the surface of the carrier particles or compact. Specifically, there may be mentioned a method of dissolving the starting compound in an appropriate solvent such as water or acetone, an inorganic acid or organic acid such as hydrochloric acid, nitric acid or acetic acid, or a solution thereof, for direct loading on the surface layer, or a method of indirect loading. Methods of direct loading include impregnation and spray methods. Methods of indirect loading include a method of first loading an (a) group compound on a carrier (first step), causing the interior (a) group compound to migrate to the surface by alkali treatment (second step) and then reducing it (third step), as in the process described above.

Loading of the (a) group compound on the carrier may be accomplished by preparing a homogeneous solution containing at least one (a) group compound, and impregnating an appropriate amount of the carrier with the solution. More specifically, the (a) group compound is dissolved in an appropriate solvent such as water or acetone or in an inorganic acid or organic acid such as hydrochloric acid, nitric acid or acetic acid to prepare a homogeneous solution, after which the carrier is impregnated therewith to obtain impregnated carrier (A). The impregnation may be followed by drying, but preferably the second step is carried out next without a drying step in order to simplify the process.

<The (d) Group Compound and Chloroauric Acid Salt>

The step of loading the (d) group compound and the chloroauric acid salt on the carrier may be accomplished in the first step either simultaneously with the (a) group compound, or separately. A more preferred loading method is one in which the (d) group compound, chloroauric acid salt and (a) group compound are simultaneously loaded in the first step.

The (d) group compound is a chloride of an element selected from copper, silver and zinc. Zinc is preferred as the element. There are no particular restrictions on the (d) group compound so long as it is a chloride of an element selected from copper, silver and zinc. It is preferably a chloride of these elements, and specifically $ZnCl_2$, $CuCl_2$ or $AgCl$.

Examples of chloroauric acid salts include $LiAuCl_4$, $NaAuCl_4$, $KAuCl_4$, $RbAuCl_4$, $CsAuCl_4$, $Mg(AuCl_4)_2$, $Ca(AuCl_4)_2$, $Sr(AuCl_4)_2$ and $Ba(AuCl_4)_2$. Preferred among these are $LiAuCl_4$, $NaAuCl_4$ and $KAuCl_4$, with $NaAuCl_4$ being especially preferred.

<Alkaline Substance>

The alkaline substance used in the second step may be supplied in the form of either a liquid or gas. It is preferably water and/or an alcohol solution. The solute may be an alkali metal hydroxide, a silicic acid compound or the like, and is preferably potassium hydroxide, sodium hydroxide, sodium metasilicate and/or barium hydroxide. In this step, all or a portion of the palladium compound may be converted to an oxide or hydroxide.

<The (b) Group Compound>

The (b) group compound is a compound comprising at least one element selected from gallium, indium, thallium, germanium, tin, lead, phosphorus, arsenic, antimony, bismuth, sulfur, selenium, tellurium and polonium. The "compound comprising at least one element" may be the element itself (metal), or a chloride, nitrate, acetate, phosphate, sulfate or oxide containing the element, or it may be a complex having an organic compound such as acetylacetonate or nitrile as the ligand.

The element in the (b) group compound is preferably gallium, germanium, tin, lead, arsenic, antimony, bismuth, selenium, tellurium or polonium, and especially tellurium or selenium.

As specific examples of (b) group compounds there may be mentioned sodium tellurite ($Na_2TeO_3$), potassium tellurite ($K_2TeO_3$), sodium tellurate ($Na_2TeO_4$), potassium tellurate ($K_2TeO_4$) and sodium selenite ($Na_2SeO_3$).

In the second step, the impregnated carrier (B) may be obtained by contacting the alkaline substance and a solution of the (b) group compound with the impregnated carrier (A). Alternatively, a solution of the alkaline substance may be contacted with the impregnated carrier (A) and then a solution of the (b) group compound contacted therewith, or in the reverse order. The solvent used is preferably water and/or an alcohol, and is most preferably water.

In the third step, a reducing substance is contacted with the impregnated carrier (B) for reduction treatment of the (a) group compound, (b) group compound, (d) group compound and chloroauric acid salt. In the reduction treatment, for example, sodium chloropalladate as the (a) group compound is reduced to palladium metal.

The reduction treatment is preferably carried out with the (a) group compound and (b) group compound loaded on the carrier. This procedure can achieve interaction with the (b) group compound while the (a) group compound is in the ion state.

The reduction treatment may also be carried out on the impregnated carrier (B) after first loading the heteropoly acid and/or its salt as the (c) group compound. That is, the fourth step and third step may be reversed. An example will be explained below.

First, the first step: a step of impregnating a carrier with a solution containing the (a) group compound, (d) group compound and chloroauric acid salt to obtain impregnated carrier (A), then the second step: a step of contacting the impregnated carrier (A) with a solution containing an alkaline substance and the (b) group compound to obtain impregnated carrier (B), the fourth step: a step of impregnating the impregnated carrier (B) with a solution containing the (c) group compound (heteropoly acid) to obtain supported catalyst (D), and the third step: a step of reduction treatment of the supported catalyst (D), are carried out in that order.

The reduction treatment may be carried out after isolating the impregnated carriers (A) and (B), or after the loading procedure. Also, optionally only a portion of the loaded (a) group compound may be reduced without reducing the entire amount.

As reducing substances there may be mentioned hydrazine, hydrogen, ethylene and carbon monoxide. By contacting these substances with the impregnated carrier (B) or supported catalyst (C) in a liquid phase or gas phase, it is possible to reduce the (a) group compound.

There are no particular restrictions on the temperature for reduction treatment carried out by a liquid phase method, but preferably the impregnated carrier (B) or supported catalyst (C) is brought to about 0-200° C. The temperature is more preferably 10-100° C.

There are also no particular restrictions on the temperature for reduction treatment carried out by a gas phase method, but preferably the impregnated carrier (B) or supported catalyst (C) is brought to about 30-350° C. The temperature is more preferably 100-300° C. When the heteropoly acid is loaded beforehand, the reaction is preferably not carried out at above 350° C. because this can result in decomposition of the heteropoly acid.

It is advantageous in practical terms from the viewpoint of equipment for the treatment pressure in reduction treatment by a gas phase method to be 0.0-3.0 MPaG (gauge pressure), but this is not particularly restrictive. The pressure is more preferably in the range of 0.1-1.5 MPaG (gauge pressure).

When a gaseous reducing substance is passed through, any reducing substance concentration may be used, and nitrogen, carbon dioxide, a rare gas or the like may be used as a diluent if necessary. The reduction may also be accomplished with ethylene, hydrogen or the like in the presence of gasified water.

Acetic acid may be produced from ethylene and oxygen by packing the catalyst into the reactor before reduction treatment and then reducing the ethylene and introducing oxygen.

A mixed gas containing a gaseous reducing substance is preferably contacted with the catalyst under standard conditions with a space velocity (hereinafter, "SV") of 10-15,000 $hr^{-1}$ and especially 100-8000 $hr^{-1}$.

The treatment system is not particularly restricted, but preferred for practical advantages is to employ a fixed bed prepared by packing the catalyst into a corrosion-resistant reaction tube.

<The (c) Group Compound: Heteropoly Acid and/or its Salt>

The heteropoly acid used for the invention is preferably a heteropoly acid comprising tungsten or molybdenum as the polyatom. As heteroatoms there may be mentioned phosphorus, silicon, boron, aluminum, germanium, titanium, zirconium, cerium, cobalt and chromium, although there is no limitation to these. Phosphorus, silicon and boron are preferred.

As specific examples of heteropoly acids there may be mentioned silicotungstic acid, phosphotungstic acid, silicomolybdic acid, phosphomolybdic acid and borotungstic acid. Preferred are the silicotungstic acid, phosphotungstic acid, silicomolybdic acid and phosphomolybdic acid compounds represented by the following chemical formulas. The structure of the polyacid is not particularly restricted, but heteropoly acids with Keggin structures are preferred.

Silicotungstic acid: $H_4SiW_{12}O_{40} \cdot nH_2O$
Phosphotungstic acid: $H_3PW_{12}O_{40} \cdot nH_2O$
Silicomolybdic acid: $H_4SiMo_{12}O_{40} \cdot nH_2O$
Phosphomolybdic acid: $H_3PMo_{12}O_{40} \cdot nH_2O$
(wherein n represents zero or an integer of 1-40)

A heteropoly acid salt used for the invention is a metal salt or onium salt obtained by substitution of all or a portion of the hydrogen atoms of the acid produced by condensation of two or more different inorganic oxygen acids. The metal replacing the hydrogens of the heteropoly acid is preferably at least one element selected from the group consisting of elements of Groups 1, 2, 11 and 13 of the Periodic Table, and the onium salt of the heteropoly acid may be an ammonium salt. Particularly preferred among these heteropoly acid salts are metal salts of lithium, sodium, potassium, cesium, rubidium, calcium, magnesium, barium, copper, gold, silver and gallium.

As preferred heteropoly acid salts, from the viewpoint of catalyst performance, there may be mentioned lithium salt of phosphotungstic acid, sodium salt of phosphotungstic acid, copper salt of phosphotungstic acid, lithium salt of silicotungstic acid, sodium salt of silicotungstic acid and copper salt of silicotungstic acid.

The (c) group compound may be a single type or a combination of two or more types. The method of loading the heteropoly acid and/or its salt on the carrier may be impregnation, spraying or the like. The solvent used for impregnation is preferably one that dissolves the (c) heteropoly acid and its salt, and water, an organic solvent or a mixture thereof may be used. More preferred for use are water, alcohols, and ethers.

The step of loading the (c) group compound onto the carrier (fourth step) is preferably carried out after the third step (reduction treatment), but it may instead be carried out before the third step as explained above. Alternatively, it may be included within the first step. That is, the (a) group compound and (c) group compound may be simultaneously loaded in the first step. Alternatively, it may be loaded separately from the (a) group compound either before or immediately after the first step.

The method for simultaneously loading the (a) group compound and (c) group compound in the first step may be a method in which the (a) group compound and (c) group compound are simultaneously loaded onto the carrier in the form of a homogeneous solution. More specifically, there may be mentioned a method in which the (a) group compound and (c) group compound are dissolved in an appropriate solvent such as water or acetone or in an inorganic acid or organic acid such as hydrochloric acid, nitric acid or acetic acid to prepare a homogeneous solution, after which the carrier is impregnated therewith and then dried. After obtaining the heteropoly acid metal salt prepared from the (a) group compound and (c) group compound, it may be dissolved in an appropriate solvent. As preferred heteropoly acids to be used in the heteropoly acid metal salt there may be mentioned phosphotungstic acid, silicotungstic acid, phosphomolybdic acid and silicomolybdic acid, while palladium may be mentioned as the metal.

As a method of loading the (c) group compound separately from the (a) group compound immediately before or after the first step, there may be mentioned a method of preparing an aqueous solution of the (a) group compound and an aqueous solution of the (c) group compound, impregnating a carrier with the (a) group compound aqueous solution or the (c) group compound aqueous solution for loading of the (a) group compound or (c) group compound, and then impregnating this with the (c) group compound aqueous solution or (a) group compound aqueous solution for loading of the (c) group compound or (a) group compound. Loading of the (a) group compound or (c) group compound may be in either order. More specifically, there may be mentioned a method in which the (a) group compound or (c) group compound is dissolved in an appropriate solvent such as water or acetone or in an inorganic acid or organic acid such as hydrochloric acid, nitric acid or acetic acid to prepare a homogeneous solution, after which the carrier is impregnated with the homogeneous solution of the (a) group compound or (c) group compound and then dried, and subsequently impregnated with the homogeneous solution of the (c) group compound or (a) group compound and dried.

<Supported Catalyst for Production of Lower Aliphatic Carboxylic Acids>

In the supported catalyst for production of lower aliphatic carboxylic acids obtained by the process for production of a supported catalyst of the invention, there are no particular restrictions on the composition of the (a) group compound, (b) group compound, (c) group compound, (d) group compound and chloroauric acid salt in the catalyst comprising (a), (b), (c), (d) and the chloroauric acid salt supported on the carrier. The preferred weight percentages in the entire supported catalyst are (a):(b):(c):(d):chloroauric acid salt=0.5-5 mass %:0.05-3.0 mass %:5-50 mass %:0.05-3.0 mass %:0.05-3.0 mass %, and especially (a): (b): (c): (d):chloroauric acid salt=1.0-2.5 mass %:0.08-1.0 mass %:10-40 mass %:0.08-1.5 mass %:0.08-1.5 mass %. When the compound groups are composed of more than one compound, the compositional ratios of each component are for their totals. The carrier and other components are also present in addition to the (a), (b), (c), (d) and chloroauric acid salt components.

The catalyst onto which the one or more compounds for the (a), (b), (c), (d) and chloroauric acid salt have been loaded as solutions may be dried by any desired method. For example, there may be mentioned a method of vacuum treatment at low temperature, and removal of the solvent by heat treatment with a hot air drier.

The loading amounts and compositional ratios of the metal element and heteropoly acid in the supported catalyst for production of lower aliphatic carboxylic acids produced according to the invention may be very precisely determined by chemical analysis using a high-frequency inductively coupled plasma (ICP) emission spectrometry device or the like, or by fluorescent X-ray analysis (XRF) or absorption spectrophotometry.

As an example of a measuring method, a prescribed amount of the catalyst is pulverized with a mortar or the like to obtain a uniform powder, and then the catalyst powder is added to an acid such as hydrofluoric acid or aqua regalis and stirred with heating for dissolution to obtain a homogeneous solution. Next, the solution is diluted to an appropriate concentration with purified water and used as the solution for analysis. The solution may be subjected to quantitative analysis by ICP.

A production process for lower aliphatic carboxylic acids using a catalyst obtained according to the invention will now be explained, with an example of using a supported catalyst of the invention to obtain acetic acid by gas phase reaction of ethylene and oxygen in a fixed bed circulating reactor, for simplicity.

In this acetic acid production process of the invention, there are no particular restrictions on the reaction temperature for production of the acetic acid by reaction of ethylene and oxygen. It is preferably 100-300° C. and more preferably 120-250° C. From the standpoint of equipment, it is advantageous in practice for the reaction pressure to be 0.0-3.0 MPaG (gauge pressure), although this is not restrictive. The pressure is more preferably in the range of 0.1-1.5 MPaG (gauge pressure).

The gas supplied to the reaction system contains ethylene and oxygen, and if necessary nitrogen, carbon dioxide or a rare gas may be used as a diluent.

For example, the ethylene is supplied to the reaction system in a proportion of 5-80 vol % and preferably 8-50 vol % while the oxygen is supplied in a proportion of 1-15 vol % and preferably 3-12 vol %, based on the total amount of the supplied gas.

Having water present in the reaction system will produce a notable effect of improving the acetic acid production activity and selectivity and maintaining catalytic activity. Water vapor is preferably present in the range of 1-50 vol % and more preferably 5-40 vol % in the reactive gas.

The ethylene starting material used in the reaction system is preferably of high purity, but there is no problem with inclusion of some amounts of lower saturated hydrocarbons such as methane, ethane and propane. The oxygen may be diluted with an inert gas such as nitrogen or carbon dioxide gas, and it may be supplied as air, for example, but when the reactive gas is circulated it is advantageous to use oxygen of high concentration, and preferably 99% or greater.

The reactive mixed gas is preferably passed through the catalyst under standard conditions with $SV=10\text{-}15{,}000\ h^{-1}$ and especially $300\text{-}8000\ h^{-1}$.

The reaction form is not particularly restricted, and any publicly known method such as using a fixed bed or fluidized bed, may be employed. Preferred for practical advantages is to employ a fixed bed prepared by packing the catalyst into a corrosion-resistant reaction tube.

The present invention will now be explained in greater detail by examples, with the understanding that the invention is not limited only to these examples.

<Pretreatment of Carrier>

All of the carriers used in the examples were dried for 4 hours in air at 110° C. as pretreatment.

<Water>

All of the water used in the examples was deionized water.

<Carrier>

All of the carriers used in the examples were silica carriers [BET area-to-weight ratio: 148 m²/g, bulk density: 405 g/l, diameter: 5 mmφ), product of Haiyuan Group]

<Starting Compounds>

Hydrochloric acid aqueous solution of sodium chloropalladate [$Na_2PdCl_4$] (product of N.E. Chemcat Corp.)

Silicotungstic acid 26-hydrate [$H_4SiW_{12}O_{40}.26H_2O$] (product of Nippon Inorganic Color & Chemical Co., Ltd.)

Phosphomolybdic acid 30-hydrate [$H_3PMo_{12}O_{40}.30H_2O$] (product of Nippon Inorganic Color & Chemical Co., Ltd.)

Zinc chloride [$ZnCl_2$] (product of Wako Pure Chemical Industries, Ltd.)

Hydrochloric acid aqueous solution of chloroauric acid [$HAuCl_4$] (product of N.E. Chemcat Corp.)

Hydrochloric acid aqueous solution of sodium chloroaurate [$NaAuCl_4$] (product of N.E. Chemcat Corp.)

Sodium metasilicate nonahydrate [$Na_2SiO_3.9H_2O$] (product of Wako Pure Chemical Industries, Ltd.)

Sodium tellurite [$Na_2TeO_3$] (product of Wako Pure Chemical Industries, Ltd.)

Sodium selenite [$Na_2SeO_3$] (product of Wako Pure Chemical Industries, Ltd.)

Hydrazine monohydrate [$N_2H_4.H_2O$] (product of Wako Pure Chemical Industries, Ltd.)

Example 1

After mixing 2.47 g of a sodium chloropalladate aqueous solution prepared to a Pd concentration of 20.24 mass %, 1.6 g of a zinc chloride aqueous solution prepared to a Zn concentration of 4.8 mass % and 1.3 g of a sodium chloroaurate hydrochloric acid aqueous solution prepared to an Au concentration of 23.13 mass % with ion-exchanged water, the mixture volume was adjusted upward with ion-exchanged water to prepare a 20 ml aqueous solution (solution A-1). A silica carrier (50 g) was impregnated with solution A-1 to absorption of the entire amount. Next, sodium metasilicate nonahydrate: 3.8 g and sodium tellurite: 70 mg were dissolved in 40 ml of ion-exchanged water to obtain an aqueous solution which was impregnated into the silica carrier, and the carrier was allowed to stand at room temperature for 20 hours. Hydrazine monohydrate: 6.5 g was added, and after gently stirring, the mixture was allowed to stand at room temperature for 4 hours. After filtering the carrier, it was transferred to a stopcock-equipped glass column and subjected to 40 hours of purified water flow for rinsing. It was then dried at 110° C. for 4 hours under an air stream to obtain impregnated carrier (A-1).

A homogeneous aqueous solution containing 10.6 g of silicotungstic acid.26$H_2O$ and 65 mg of phosphomolybdic acid.30$H_2O$ was also prepared and the volume was adjusted upward to 20 ml (solution B-1). The previously prepared impregnated carrier (A-1) was impregnated with solution B-1 to absorption of the total amount. It was then dried at 110° C. for 4 hours under an air stream to obtain catalyst 1 for production of acetic acid.

Example 2

Catalyst 2 for production of acetic acid was obtained in the same manner as Example 1, except that 43.8 mg of sodium selenite was used instead of the 70 mg of sodium tellurite.

Example 3

After mixing 2.47 g of a sodium chloropalladate aqueous solution prepared to a Pd concentration of 20.24 mass %, 1.3 g of a zinc chloride aqueous solution prepared to a Zn concentration of 4.5 mass % and 0.87 g of a sodium chloroaurate hydrochloric acid aqueous solution prepared to an Au concentration of 23.13 mass % with ion-exchanged water, the mixture volume was adjusted upward with ion-exchanged water to prepare a 20 ml aqueous solution (solution A-3). A silica carrier (50 g) was impregnated with solution A-3 to absorption of the total amount. Next, sodium metasilicate nonahydrate: 8.0 g and sodium tellurite: 200 mg were dissolved in 90 ml of ion-exchanged water to obtain an aqueous solution which was impregnated into the silica carrier, and the carrier was allowed to stand at room temperature for 20 hours. Hydrazine monohydrate: 6.5 g was added, and after gently stirring, the mixture was allowed to stand at room temperature for 4 hours. After filtering the carrier, it was transferred to a stopcock-equipped glass column and subjected to 40 hours of purified water flow for rinsing. It was then dried at 110° C. for 4 hours under an air stream to obtain impregnated carrier (A-3).

Separately, 20.7 g of silicotungstic acid 26-hydrate was prepared as a homogeneous aqueous solution and adjusted upward to 45 ml (solution B-3). The previously prepared impregnated carrier (A-3) was impregnated with solution B-3 to absorption of the total amount. It was then dried at 110° C. for 4 hours under an air stream to obtain catalyst 3 for production of acetic acid.

Comparative Example 1

Catalyst 4 for production of acetic acid was obtained in the same manner as Example 1, except that 3.0 g of a chloroauric acid hydrochloric acid aqueous solution prepared to an Au concentration of 10 mass % with ion-exchanged water was used instead of the 1.3 g sodium chloroaurate hydrochloric acid aqueous solution.

Comparative Example 2

Catalyst 5 for production of acetic acid was obtained in the same manner as Example 3, except that 4.0 g of a chloroauric acid hydrochloric acid aqueous solution prepared to an Au concentration of 10 mass % with ion-exchanged water was used instead of the 0.87 g sodium chloroaurate hydrochloric acid aqueous solution.

Figure 1:
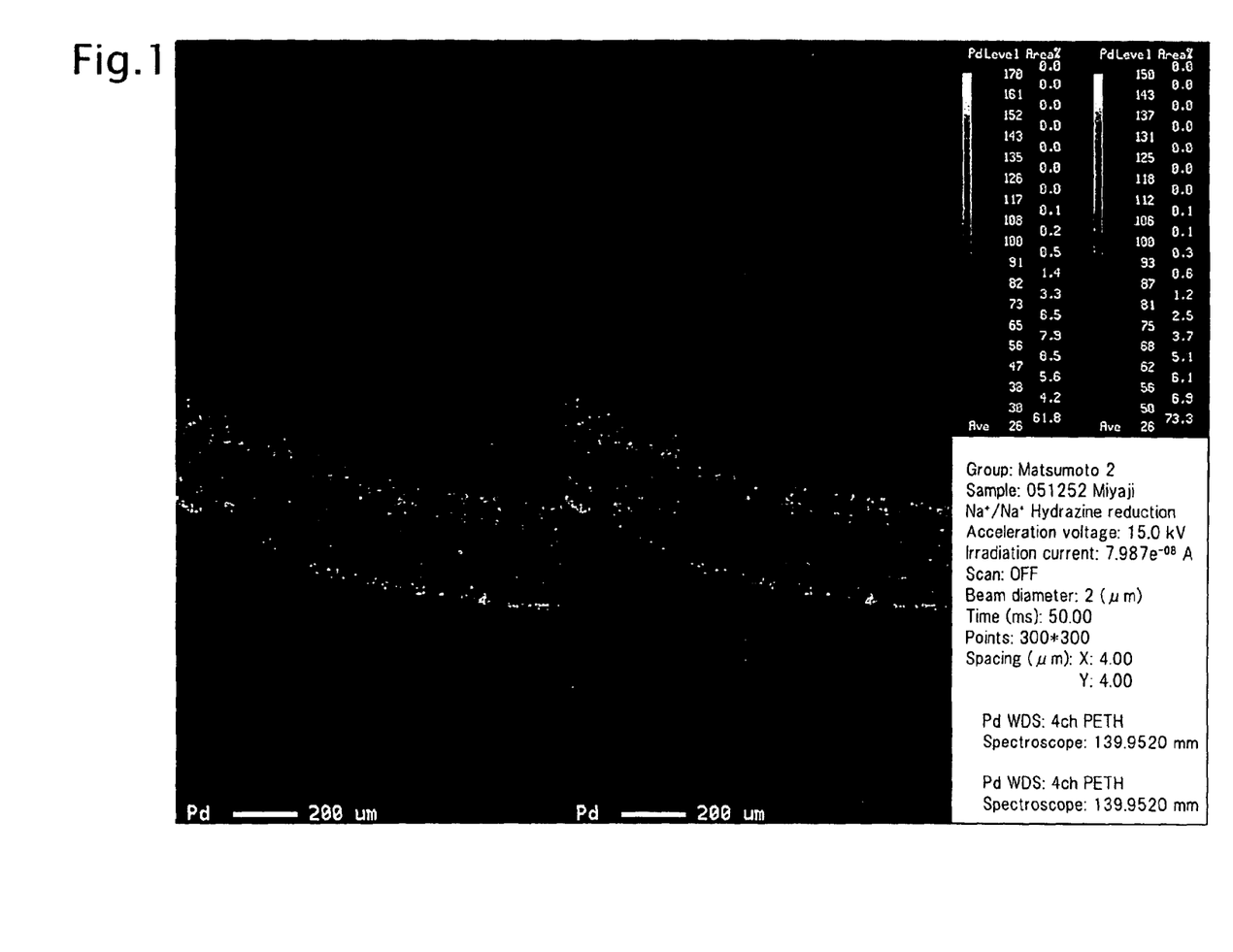
FIG. 1 is an EPMA profile for catalyst 1 obtained in Example 1.
Figure 2:
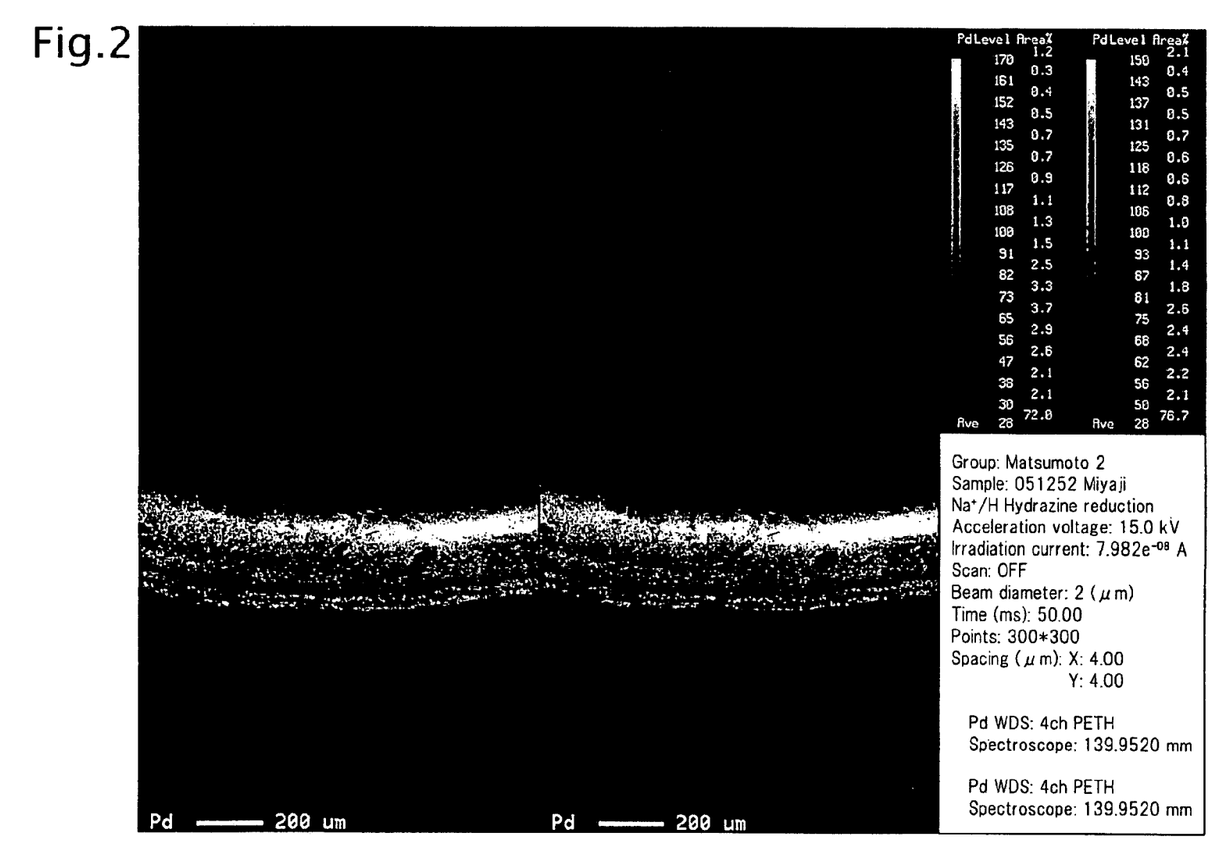
FIG. 2 is an EPMA profile for catalyst 4 obtained in Comparative Example 1.

Catalyst 1 for production of acetic acid (Example 1) and catalyst 4 for production of acetic acid (Comparative Example 1) were subjected to EPMA measurement (JXA8900, product of JEOL Corp.) using the cross-section that gave the maximum cross-sectional area of catalyst particles for each. The EPMA profiles are shown in FIG. 1 and FIG. 2. FIG. 1 shows that the catalyst of Example 1 had the palladium distributed more evenly in the eggshell than Comparative Example 1.

Example 4, Example 5 and Comparative Example 3

After uniformly diluting 5 ml each of catalyst 1 for production of acetic acid obtained in Example 1, catalyst 2 for production of acetic acid obtained in Example 2 and catalyst 4 for production of acetic acid obtained in Comparative Example 1 with 11 ml of silica, each was packed into a SUS316L reaction tube (inner diameter: 25 mm), and a mixed gas comprising ethylene:oxygen:water:nitrogen in a volume ratio of 10:6:25:59 was introduced at a space velocity of 9000 $h^{-1}$, with a catalyst layer reaction peak temperature of 200° C. and a reaction pressure of 0.8 MPaG (gauge pressure), for reaction between the ethylene and oxygen to obtain acetic acid.

Analysis of the reaction was accomplished by cooling the total amount of the exit gas that had passed through the catalyst-packed layer, collecting the total amount of the collected condensed reaction solution and performing analysis by gas chromatography. The composition of the remaining non-condensed gas was analyzed by gas chromatography after measuring the total amount of non-condensed gas flowing out during the sampling time and sampling a portion thereof. The product gas was cooled, and the cooled condensed solution and gas component were analyzed by gas chromatography (GC-14B by Shimadzu Corp., FID detector: TC-WAX capillary column (length: 30 m, inner diameter: 0.25 mm, film thickness: 0.25 μm)).

The catalyst activity was calculated as the mass of acetic acid per hour produced per catalyst volume (liters) (space-time yield: STY, units: g/hL$_{cat}$). The carbon dioxide selectivity was determined by the following formula.

Carbon dioxide selectivity (based on carbon atom)(%)
=(number of carbon atoms in carbon dioxide/
number of carbon atoms in total product)×100

The values for acetic acid STY and carbon dioxide selectivity at the start of the reaction are shown in Table 1. Table 1 shows that the catalysts of Example 1 and Example 2 are superior to the catalyst of Comparative Example 1 in terms of improvement in the acetic acid STY and reduction in carbon dioxide selectivity.

TABLE 1

| | Catalyst | Acetic acid STY/g h$^{-1}$L$^{-1}$ | Carbon dioxide selectivity/% |
|---|---|---|---|
| Example 4 | Catalyst 1 | 513.6 | 6.4 |
| Example 5 | Catalyst 2 | 527.1 | 7.0 |
| Comp. Ex. 3 | Catalyst 4 | 451.3 | 8.1 |

Example 6 and Comparative Example 4

After uniformly diluting 50 ml each of catalysts 3 and 5 for production of acetic acid obtained in Example 3 and Comparative Example 2 with 150 ml of silica, each was packed into a SUS316L reaction tube (inner diameter: 27 mm), and a mixed gas comprising ethylene:oxygen:water:nitrogen in a volume ratio of 10:6:25:59 was introduced at a space velocity of 4000 $h^{-1}$, with a catalyst layer reaction peak temperature of 210° C. and a reaction pressure of 0.68 MPaG (gauge pressure), for reaction between the ethylene and oxygen to obtain acetic acid.

The same analysis as in Example 4 was performed to determine the acetic acid STY at the start of the reaction and at 1000 hours after start of the reaction. The reduction in acetic acid STY during that time was also determined by the following formula.

Reduction in acetic acid STY per 1000 hours={
($STYy$)-($STYx$)}×1000/($y$-$x$)

X: reaction time (start of reaction)
Y: reaction time (after approximately 1000 hours)

The acetic acid STY at the start of the reaction and at 1000 hours after start of the reaction, and the reduction in acetic acid STY during that time, are shown in Table 2. The results in Table 2 show that the catalyst of Example 6 exhibited more excellent inhibition of catalyst performance deterioration than Comparative Example 4.

TABLE 2

| | Catalyst | Acetic acid STY (gh$^{-1}$L$^{-1}$) Initial | After 1000 hours | Reduction in acetic acid STY after 1000 hours (gh$^{-1}$L$^{-1}$) |
|---|---|---|---|---|
| Example 6 | Catalyst 3 | 551.3 | 410.8 | 140.5 |
| Comp. Ex. 4 | Catalyst 5 | 553.6 | 338.2 | 165.4 |

INDUSTRIAL APPLICABILITY

According to the invention, the obtained supported catalysts can be used to improve production volume of lower aliphatic carboxylic acids and inhibit carbon dioxide gas by-product in the production of lower aliphatic carboxylic acids by reaction between lower olefins and oxygen, and it is therefore industrially useful.

The invention claimed is:

1. A process for production of a supported catalyst to be used for production of a lower aliphatic carboxylic acid from a lower olefin and oxygen, characterized by comprising the following first, second and third steps in order First step
A step of impregnating a carrier with a solution containing at least one compound comprising at least one element selected from elements of Groups 8, 9 and 10 of the Periodic Table (hereinafter referred to as (a) group compound), at least one chloride of an element selected from copper, silver and zinc (hereinafter referred to as (d) group compound), and an alkali metal salt of chloroauric acid, to obtain an impregnated carrier (A)

Second step
A step of contacting the impregnated carrier (A) with an alkaline substance and a compound comprising at least one element selected from gallium, indium, thallium, germanium, tin, lead, phosphorus, arsenic, antimony, bismuth, sulfur, selenium, tellurium and polonium (hereinafter referred to as (b) group compound) to obtain impregnated carrier (B) (where the alkaline substance and the (b) group compound may be contacted with impregnated carrier (A) either simultaneously or separately)

Third step
A step of contacting impregnated carrier (B) with a reducing substance to obtain supported catalyst (C).

2. The process for production of a supported catalyst according to claim 1, which further comprises a step of loading at least one compound selected from heteropoly acids and their salts (hereinafter referred to as (c) group compound) on the carrier.

3. The process for production of a supported catalyst according to claim 2, wherein the polyatom of the heteropoly acid and/or its salt as (c) group compound is tungsten and/or molybdenum.

4. The process for production of a supported catalyst according to claim 2, wherein the heteroatom of the heteropoly acid and/or its salt as the (c) group compound is at least one element selected from phosphorus, silicon and boron.

5. The process for production of a supported catalyst according to claim 2, wherein the heteropoly acid and/or its salt as the (c) group compound is at least one compound selected from silicotungstic acid, phosphotungstic acid, silicomolybdic acid, phosphomolybdic acid and salts thereof.

6. The process for production of a supported catalyst according to claim 2, wherein the (d) group compound is zinc chloride.

7. The process for production of a supported catalyst according to claim 1, wherein the (d) group compound is zinc chloride.

8. The process for production of a supported catalyst according to claim 1, wherein the (a) group compound is a compound comprising at least one element selected from ruthenium, osmium, rhodium, iridium, palladium and platinum.

9. The process for production of a supported catalyst according to claim 1, wherein the (b) group compound is a compound comprising at least one element selected from gallium, germanium, tin, lead, bismuth, selenium and tellurium.

10. A supported catalyst for production of acetic acid by reaction between ethylene and oxygen, which is produced by a process according to claim 1.

* * * * *